(12) United States Patent
Leschinsky

(10) Patent No.: US 9,950,009 B2
(45) Date of Patent: Apr. 24, 2018

(54) TREATMENT METHODS AND BIOLOGICALLY ACTIVE PREPARATIONS USING BLOOD OF A DONOR SUBJECTED TO REMOTE CONDITIONING

(71) Applicant: LifeCuff Technologies Inc., Waldwick, NJ (US)

(72) Inventor: Boris Leschinsky, Mahwah, NJ (US)

(73) Assignee: LifeCuff Technologies Inc., Waldwick, NJ (US)

( * ) Notice: Subject to any disclaimer, the term of this patent is extended or adjusted under 35 U.S.C. 154(b) by 0 days.

(21) Appl. No.: 15/431,443

(22) Filed: Feb. 13, 2017

(65) Prior Publication Data

US 2017/0151280 A1 Jun. 1, 2017

Related U.S. Application Data

(63) Continuation-in-part of application No. PCT/US2015/044816, filed on Aug. 12, 2015.

(51) Int. Cl.
| | |
|---|---|
| A61K 35/14 | (2015.01) |
| A61B 17/132 | (2006.01) |
| A61M 1/02 | (2006.01) |
| A61M 1/34 | (2006.01) |
| A61M 1/36 | (2006.01) |
| A61N 1/36 | (2006.01) |

(52) U.S. Cl.
CPC .......... *A61K 35/14* (2013.01); *A61B 17/1325* (2013.01); *A61M 1/0259* (2013.01); *A61M 1/34* (2013.01); *A61M 1/3403* (2014.02); *A61M 1/3406* (2014.02); *A61M 1/36* (2013.01); *A61M 1/3681* (2013.01); *A61M 1/3687* (2013.01); *A61M 1/3693* (2013.01); *A61N 1/36* (2013.01); *A61M 2205/3306* (2013.01); *A61M 2205/3368* (2013.01)

(58) Field of Classification Search
None
See application file for complete search history.

(56) References Cited

U.S. PATENT DOCUMENTS

| | | | | |
|---|---|---|---|---|
| 2006/0257496 | A1* | 11/2006 | Shestakov | A61K 35/16 424/531 |
| 2007/0110817 | A1* | 5/2007 | Shestakov | A61K 9/0019 424/531 |

OTHER PUBLICATIONS

Lim SY, Hausenloy DJ. Remote ischemic conditioning: from bench to bedside. Frontiers in Physiology, vol. 3, article 27, Feb. 2012.
Sakai H et al. Removal of cellular-type hemoglobin-based oxygen carrier (hemoglobin-vesicles) from blood using centrifugation and ultrafiltration. Abstract. Artificial Organs, 36(2):202-9, Feb. 2012.
Gay M et al. Proteomic analysis of polypeptides captured from blood during extracorporeal albumin dialysis in patients with cholestasis and resistant pruritus. PLOS ONE, vol. 6, Issue 7, e21850, Jul. 2011.
Murry CE, Jennings RB, Reimer KA. Preconditioning with ischemia: a delay of lethal cell injury in ischemic myocardium. Abstract. Circulation 74(5):1124-36, Nov. 1986.

* cited by examiner

*Primary Examiner* — Ralph J Gitomer
(74) *Attorney, Agent, or Firm* — Boris Leschinsky

(57) ABSTRACT

Treatment methods are described using blood collected from a donor after subjecting thereof to remote conditioning such as remote ischemic conditioning via several episodes of short-term limb occlusion. Blood containing remote conditioning substances or a biologically active preparation containing such substances may be stored and used at a future time to afford a health benefit to the treatment subject. Extraction of remote conditioning substances may be done extracorporeally using dialysis or other blood processing methods following by returning of blood to the donor. Extraction of remote conditioning substances may be done during the time periods of their maximum presence in donor blood.

12 Claims, No Drawings

TREATMENT METHODS AND BIOLOGICALLY ACTIVE PREPARATIONS USING BLOOD OF A DONOR SUBJECTED TO REMOTE CONDITIONING

CROSS REFERENCE DATA

The present invention claims priority benefit from a U.S. Provisional Patent Application No. 6241037 with the same title filed 23 Aug. 2014. This application is a continuation-in-part of the PCT Application No. PCT/US15/44816 with the same title filed 12 Aug. 2015. The content of these applications is incorporated herein in its entirety by a respective reference.

BACKGROUND OF THE INVENTION

The present invention relates generally to treatment methods using donor blood and preparations made from donor blood. More particularly, the invention describes subjecting a donor to a remote conditioning procedure prior to collecting or processing blood therefrom. As a result of such procedure, blood and blood-derived products obtained from the donor may contain certain biologically active substances. When administered to a treatment subject, these substances may provide a clinically desired health effect or trigger further release of substances causing a health benefit such as for example systemic protection against ischemia-reperfusion injury or reducing systemic inflammation.

In the broadest context, the term "conditioning" is defined as the use of stress to yield an improved health outcome. The best known example of conditioning is physical exercise, which of course yields multiple health benefits. Another example is fasting or alternate-day fasting, which also induces many health benefits including a number of reduced disease susceptibilities. For the purposes of this description, the term "conditioning" is defined in a narrower medical context to mean the application of a controlled biological stress to obtain a specific health benefit, mitigate against an anticipated negative health effect including an effect from an anticipated extended biological stress applied at a later time. Furthermore, the term "remote conditioning" is used herein to describe a plurality of repeated intermittent applications of a sub-lethal controlled biological stress to a suitable tissue bed or the whole body of a subject. Importantly, these repeated intermittent applications of controlled biological stress are conducted over predefined periods of time and alternated with predefined periods of time when the biological stress is withdrawn—so as to allow for a biological recovery to take place inbetween applications of the biological stress. The notion of "remote" in the term "remote conditioning" is used to define the circumstances where the health benefit is defined in a tissue bed or an organ other than the tissue bed, which is used to apply the biological stress, which may also include the whole body.

Transfusions of whole blood and blood components and products derived from whole blood are broadly known to provide a great deal of health benefit to subjects in need thereof. Examples of such treatments include blood transfusions to subjects experiencing moderate to severe blood loss. Transfusions of platelets, plasma, or red blood cells are widely used to elevate depressed blood pressure, improve organ perfusion and restore homeostasis in subjects with reduced blood volume or reduced cell count. Yet such transfusions are known to also cause a massive systemic inflammatory response throughout the body of the recipient. Intra-operative blood transfusions for example are known to cause a release of inflammatory mediators in various vascular beds. There is a need for treatment methods and blood-derived products that are designed to minimize such negative effects of traditional blood transfusions.

Remote conditioning is generally known to provide a variety of health benefits to the same subject that it is applied to. One known example is remote ischemic conditioning in which a series of intermittent occlusions of blood flow to a suitable tissue bed (for example a leg or an arm of the subject) is known to provide protection against subsequent ischemia-reperfusion injury. For patients with a heart attack for example, such therapy has been shown to significantly reduce the size of the final myocardial infarction.

Direct application of remote conditioning to a treatment subject has a number of limitations. In emergency circumstances—for example for a subject with severe blood loss as a result of an accident or trauma—there is a need for an immediate initiation of blood transfusion to restore organ perfusion and relieve hypotension. There is no time available to conduct a traditional remote conditioning procedure, which lasts typically 40 min or so. After the blood transfusion is initiated, the inflammatory reaction may soon be triggered and so applying a traditional remote conditioning procedure may not provide the desired effect or may not achieve its full therapeutic potential. Other circumstances when direct application of remote conditioning to the treatment subject is difficult may be the situations of severe trauma in which access to a tissue bed suitable for applying remote conditioning may not be available.

Accordingly, there is a need to overcome the limitations of the prior art and to provide treatment methods and blood-derived products designed to minimize inflammation or other negative health consequences upon their immediate use, while providing immediate and full health benefits to the treatment subject.

SUMMARY OF THE INVENTION

Accordingly, it is an object of the present invention to overcome these and other drawbacks of the prior art by providing novel treatment methods and biologically active preparations using a blood from a donor subjected to remote conditioning prior to collecting blood therefrom.

It is another object of the present invention to provide novel biologically active preparations derived from the blood of the donor after subjecting the donor to remote conditioning, such preparations may be produced by processing donor blood using an intracorporeal or an extracorporeal apparatus, followed in some instances by returning blood to the donor after such processing.

It is a further object of the present invention to provide novel biologically active preparations derived from one or several donors after subjecting at least one of the donors to remote conditioning, such preparations may be prepared by pooling together blood or blood-derived products from a group of such donors.

It is yet a further object of the present invention to provide novel biologically active preparations derived from non-human donors after subjecting thereof to remote conditioning.

The novel treatment methods of the invention include identifying one or more donors and subjecting this one donor or multiple donors to a procedure of remote conditioning prior to collecting or processing blood therefrom. According to the present invention, at least one or more remote conditioning substances may be released into the blood stream of the donor as a result of application of remote conditioning. Collected blood, blood components, blood-derived products or extracted remote conditioning substance may be obtained from the donor, optionally stored, and then administered to the treatment subject to derive the desired health benefit. The ready presence of remote conditioning substances in the blood or a blood-derived product administered to the treatment subject may be used to reduce inflammation, attenuate ischemia-reperfusion injury or provide other health benefits immediately or soon after administration of such transfusions—without the need for a time-consuming procedure of conducting remote conditioning therapy on the treatment subject directly.

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

The present invention is generally concerned with enhancing donor blood or a blood product derived therefrom by subjecting the donor to a procedure of remote conditioning prior to collecting or processing donor blood. Remote conditioning may be applied to the donor by subjecting thereof to repeated applications of at least one biological stress.

Remote Conditioning Timing Considerations

Applications of the biological stress may be activated for predefined periods of time and may be alternated with predefined periods of time when the biological stress is withdrawn. Periodic cessation of applying the biological stress may allow the body of the donor to recover and biologically adapt to the applied stress by releasing at least one or likely a plurality of beneficial remote conditioning substances into the blood stream. Collecting blood containing such remote conditioning substances or deriving a biologically active preparation from such blood may provide additional health benefits for the subject of treatment at a later time when such blood is transfused or the product is administered thereto.

According to the present invention, a single application of the biological stress may not be sufficient to cause a desired release of remote conditioning substances in the blood stream of the donor. Repeated applications of the biological stress alternated with periods of biological recovery may be needed to fully activate this process. In embodiments, the number of such applications of the biological stress may be anywhere between two and ten. In other embodiments, the number of applications of the biological stress may be three times, four times, five times, or six times.

A duration of time when the biological stress is applied may vary depending on the nature of the biological stress. For example, for ischemic stress, hypoxia, or changing temperature, such duration of stress may be from about 30 seconds to about 20 minutes. For radiation exposure, such duration may be a small fraction of a second. The term "about" is used herein to mean plus or minus ten percent of the cited parameter. In embodiments, for an ischemic stress, the duration of its application may also be a function of a specific tissue bed to which such ischemic stress is applied. For a limb of the donor, such ischemic stress may be applied for at least one minute at a time. In embodiments, each application of ischemic stress to the limb of the donor may be lasting for two minutes, three minutes, four minutes, five minutes, six minutes, seven minutes, eight minutes, nine minutes, ten minutes, or any duration of time inbetween these durations.

The duration of applying the biological stress may be even between repetitive applications or uneven. In embodiments, the first duration of applying the biological stress may be longer then subsequent durations. In other embodiments, each duration of applying the biological stress may vary starting from minimal time when biological response may be initially detected and extending to the maximal time when the biological response has reached its maximum.

The duration of time when the biological stress is withdrawn may generally vary from a minimal time when at least some degree of biological recovery may be detected and extending to the maximum time when repeating the application of the biological stress is no longer effective and treated by the body of the donor as a de-novo stress. This may be the case when remote conditioning substances are downregulated to be close to their native dormant levels for example. Such periods of cessation of the biological stress may be even or uneven between applications of the stress and may depend on the nature of the biological stress itself. For example, for ischemic stress, the periods of cessation of ischemia and restoration of blood flow may vary between about 30 seconds and 20 minutes. In other embodiments, such periods of ischemia withdrawal may vary between about 3 minutes and ten minutes. For other types of the biological stress, the periods of biological recovery may take much longer. For example, for exposure to radiation or exposure to a toxic substance, the period of biological recovery may take hours, days or even weeks.

Importantly, both the periods of applying the biological stress and the periods of withdrawal of the biological stress may be selected to assure no lasting or permanent damage is done to the selected tissue bed of the whole body of the donor as a result of applying the biological stress. In that sense, the biological stress may be described as sub-lethal.

Another consideration in selecting the proper way to apply the biological stress for the purposes of remote conditioning is the degree of the stress itself. Such degree may vary from having the biological stress being minimally effective to the degree when further increase may not cause an increase in remote conditioning efficacy or the stress may no longer be considered sub-lethal. For example, the degree of ischemic stress may be varied by the size of the tissue bed subjected to the ischemia. It is generally believed that a temporary occlusion of a blood flow to a small tissue bed (a finger for example) may not be sufficient to cause a systemic remote conditioning response, while applying the ischemic stress to more than one limb may not cause an additional increase in efficacy in comparison with a single limb application thereof.

A further timing consideration according to the present invention is when to collect blood or extract the remote conditioning substance from the donor following the donor being subjected to remote conditioning. According the invention, the blood of the donor may be enhanced by the presence of remote conditioning substances or humoral factors released as a result of remote conditioning. The process of such release may be complex. More than one beneficial remote conditioning substance may be released to reach its respective peak at various times.

According to the present invention, collection of blood or extracting the remote conditioning substance may be conducted at the time when the release of the desired substance is at its peak or during a window of time when the remote conditioning substance is circulated in the blood stream of the donor in concentrations sufficient for making the treatment using donor blood sufficiently effective for the treatment subject.

Depending on the type of biological stress used for eliciting remote conditioning to the donor, there may be more than time window to collect blood from the donor or extract the remote conditioning substance. For example, for remote conditioning done using ischemic stress, a first period of time to do so may be during the first so-called "window of protection" and a second period of time may be during the second window of protection. In embodiments, the first window of protection may start from the time of completion of remote conditioning (or shortly before then, for example after completion of 50% or 75% of remote conditioning) and last for up to six hours afterwards. In other embodiments, such first period of time may commence upon completion of remote conditioning and last for two hours afterwards. The second period of time for the second window of protection may start from about 24 hours following the completion of remote conditioning and last for up to 96 hours afterwards. The delay in the onset of the second window of protection may be explained by the nature thereof, which is dependent on changing gene expressions and the internal synthesis of certain proteins, a process that takes time to be effective.

Other types of the biological stress may necessitate other windows of time for collecting or processing donor blood. In embodiments, such period of time may generally start at the completion of remote conditioning and extend for up to 6 hours afterwards.

In embodiments, the time for blood collection or extracting the remote conditioning substance may be selected based not only on the time elapsed after administration of remote conditioning but also based on direct or indirect monitoring of the level of desired remote conditioning substance or a substance known to trigger the release thereof in the blood stream. Such monitoring may be done continuously (by using an indwelling blood sensor probe) or intermittently by taking blood samples and analyzing them outside the body of the donor and using blood analyzing equipment. Such blood samples may be taken from the donor at predefined periods of time, such as for example hourly in the first 4-6 hours after completion of remote conditioning.

The method of the present invention further takes into account that blood collection or blood processing may take some time as it is preferably done through a small diameter needle. To maximize the efficacy of the method, the start time for such blood collection or processing may commence as soon as the concentration of the desired remote conditioning substance has reached a minimally acceptable level, such as at the beginning of the first window of protection or the second window of protection as described above. Completion of blood collection or blood processing may be extended to about the end of the first window of protection or respectively the second window of protection—with the understanding that further collection of blood may not have sufficient concentration of remote conditioning substance to be of clinical value. Of course, more blood may be collected for general blood donation purposes if clinically feasible. In that case however, additional blood may be separated from the blood collected during the first or the second window of protection so as not to dilute thereof and preserve the health benefit associated with remote conditioning.

The amount of blood collected from the donor may vary but in general may follow traditional practices of donor blood collection. Typically, one unit of blood may be collected from the donor in a single blood donation session.

Such blood collection or blood processing sessions may be repeated from time to time, and may be preceded by one or more applications of remote conditioning. In embodiments, following a single application of remote conditioning a first volume of blood may be collected during the first period of time when at least some remote conditioning substances are known to be at sufficiently high concentration levels; and the second volume of blood may be collected during the second period of time when other remote conditioning substances are known to reach sufficiently high concentration levels to be clinically useful for subsequent administration to the treatment subject. The second volume of blood may be collected days later after the first volume of blood is obtained. In other words, a single application of remote conditioning may be followed by more than one blood collection process or more than one blood processing for extracting desired remote conditioning substances. Additional remote conditioning may be applied to the donor at various time intervals such as for example just prior to additional blood donations—so as to boost the level of circulating remote conditioning substances.

In further embodiments, remote conditioning may be repeatedly applied on a scheduled basis so that the donor has a continuously high level of circulating remote conditioning substances. In addition to providing health benefits to the donor, this method may allow for blood donation or blood processing to be done at any time or even on demand, when it is most urgently needed—such as for example for direct blood transfusions to the treatment subject.

Types of Biological Stresses Suitable for Remote Conditioning

In embodiments, a variety of biological stresses may be suitable for the purposes of applying remote conditioning to the donor. The application of remote conditioning may be conducted using a repetitive single biological stress or by applying more than one biological stress—either one at a time or by more than one biological stresses applied consecutively, in an overlapping manner or in parallel to each other.

In embodiments, application of the biological stress may be tightly controlled—at least in terms of the timing and their intensity as described above as well as in the below portions of this description. The following discussion illustrates various suitable biological stresses in greater detail.

Ischemic stress is a known biological stress suitable for inducing remote conditioning. Intermittent periods of substantial reduction or full cessation of blood flow to a suitable tissue bed is known to cause a protective remove conditioning effect in a subject to which it is applied. In embodiments, blood flow may be reduced to a level of 10 percent or less of the normal unobstructed blood flow to the same tissue bed. Interruption of blood flow may be conducted a number of times, such as any number of times between two and ten. The duration of each blood flow interruption may vary from 30 seconds to 20 min and may be either the same or different between successive episodes of ischemic stress. Restoration of blood flow inbetween the periods of blood flow occlusion allows for adaptive biological response and may last anywhere from about 1 minute to about 20 minutes. In a typical scenario, blood flow to a limb of the donor may be interrupted non-invasively by using an inflatable cuff placed about that limb and applying sufficient air pressure to the cuff so as to cause limb ischemia. Three or four cycles of 5 min limb occlusions alternated with 5 min of limb release may constitute a sufficient procedure of remote conditioning.

In addition to using a manually inflated blood pressure cuff, a variety of devices are known in the art to be configured for automated periodic cuff inflations and deflations for the purposes of applying remote ischemic conditioning to a subject. Examples of such devices are discussed in my U.S. Pat. Nos. 8,114,026; 8,753,283; and 8,795,323 incorporated herein in their respective entireties by reference. Such devices may be used for the purposes of one of the steps of this invention in order to apply remote conditioning to the donor.

A significant practical advantage of using a non-invasive method of applying remote ischemic conditioning with an inflatable cuff is that it can be seamlessly incorporated with the process of collecting blood from a donor in a typical blood bank. Such donor facility may have a number of donor stations equipped with device for applying non-invasive remote conditioning to the donor prior to blood donation. Such devices may also be configured for measuring blood pressure or other parameters needed to be monitored before, during or after blood donation.

In embodiments useful for this and other biological stresses described below, such inflatable cuff devices may also be configured to have a "Vein Identification" mode with low pressure inflation designed to only cause venous blood flow restriction or occlusion and not the occlusion of the artery. When operated in that mode, these devices may be used in place of a rubber band or a manual tourniquet—in order to identify a vein to ease the vein cannulation process. To achieve the vein restriction or occlusion, the air pressure in the cuff may be increased to sub-arterial levels, for example in the range from about 20 mmHg to about 80 mmHg. Continuing flow of arterial blood past the cuff will fill up the veins and cause their engorgement so they can be easily seen and cannulated by the medical personnel.

In a further improvement, the devices equipped with an inflatable cuff may be used in "Increase Blood Flow" mode to enhance blood collection or processing using a small bore needle. Such small diameter needle creates a certain level of resistance to blood flow therethrough, which may extend the time of blood collection. To increase blood flow through the needle, the vein pressure may be artificially increased only during the blood collection or extracorporeal processing part of the process. An increase in venous blood pressure may be caused by inflating the cuff at a point proximal to the needle placement so as to controllably restrict blood flow return to the heart. Restricted venous return will cause an increase of venous pressure and cause an increase of blood flow through the needle. In embodiments, the cuff may be placed on an upper arm or a thigh of the donor and inflated to a cuff pressure of about 10 mmHg to about 80 mmHg or any pressure therebetween for at least a portion of the duration of blood collection or blood processing procedure. This mode of operation may be advantageous to reduce blood collection or processing time, allow use of a smaller diameter needle or increase the volume of blood available for processing. It may also be advantageous to reduce processing time in case of prolonged extracorporeal extraction of remote conditioning substances as well as to fit such time within a respective first or second window of protection while continuing to use small bore needles for blood access and optional blood return.

Remote ischemic conditioning may also be applied using an indwelling device with an inflatable internal balloon configured for arterial occlusion, as is also described for example in my U.S. Pat. No. 8,114,026. One advantage of using such a device is that arterial blood withdrawal may be conducted using the same device—once remote conditioning is completed.

Hypoxia is another biological stress, which may be repeatedly administered to the donor. Hypoxic remote conditioning may be administered by intermittently lowering the oxygen content in the air, which is breathed in by the donor. Normal oxygen content in air is about 21 percent. Techniques and breathing devices are known to allow reduction of oxygen content to a therapeutically beneficial but still sub-lethal level, such as for example between 10 percent and 16 percent. Air with reduced oxygen content may be supplied to the donor through a breathing mask or the donor may be placed into a small confined space filled with such air. Hypoxic remote conditioning may be applied by breathing intermittently through the mask and alternating with normal breathing of ambient air. Alternatively, the donor may enter the confined space to breathe low oxygen air for predetermined periods of time and alternate with breathing ambient air outside such confined space.

Periods of time for breathing low oxygen air as well as normal ambient air may vary from a few minutes such as 3-10 minutes to a few hours at a time. Three to ten cycles of hypoxic conditioning may be applied. In embodiments, a sleeping tent may be provided for the donor to sleep in the night before blood collection or processing. Such sleeping tent or enclosure may be equipped with a device to vary oxygen content based on a predetermined hypoxic conditioning protocol.

In embodiments, hypoxic conditioning may be applied using normal atmospheric pressure or reduced atmospheric pressure, such as to simulate high altitude/low oxygen conditions. To achieve this at sea level, a hypobaric chamber may be used to induce donor breathing at periodically lowered atmospheric pressure combined or overlapped with intermittent drops in oxygen content according to the predefined hypoxic conditioning treatment protocol. The extent of lowering ambient pressure may be to simulate high altitude conditions from about 5,000 feet to about 15,000 feet.

Change in temperature may be used as a biological stress for the present invention. Such change may be applied as an intermittent increase in body temperature by applying heat to the donor; or as an intermittent cooling of the body temperature by applying cold to the donor; or as an intermittent combination of heating alternated with cooling.

The extent of temperature elevation may be adjusted from normal body temperature of 37 degrees C. to about 43 degrees C. so as not to exceed natural "high fever" conditions. The extent of lowering body temperature may be from the same normal level down to about 32-35 degrees C., also known as mild hypothermia. In embodiments, body temperature may be reduced until the onset of shivering and then slightly raised to avoid such shivering.

The predetermined periods of time for induction and withdrawal of temperature change as a way to apply thermal remote conditioning may be from 3-5 minutes to 1-2 hours at a time. Three to ten cycles of temperature change may be applied to the donor for the purposes of thermal remote conditioning.

While the body temperature may be regulated using indwelling catheters with built-in heat exchangers, it may be beneficial to use non-invasive equipment to cause a change in body temperature. In some embodiments, heat lamps, heating mattresses and heating blankets may be used to intermittently raise body temperature of the donor. In other embodiments, skin contacting pads may be placed in close contact with the body of the donor and warming or cooling fluid may be circulated therethrough to cause respective increase or decrease of skin temperature. Sufficient skin exposure to such pads may be needed to cause rapid enough warming or cooling of the donor body. A combination of the torso, back, thigh, and optionally arm pads may be used to achieve sufficient skin exposure.

In further embodiments, the body of the donor may be submerged into a bath with a circulating fluid. The temperature of such fluid may be intermittently changed by a controller according to the predefined remote conditioning protocol.

Electrical stimulation of suitable target nerves or tissue beds is a suitable biological stress for the present invention. Such stimulation may be applied using internal electrodes or external skin electrodes. It may also be applied using electro-acupuncture needles or electrodes, such as for example described in the U.S. Pat. No. 6,836,686 incorporated herein by reference. For safety reasons, external skin electrodes may be preferred. In embodiments, electrical stimulation may be applied intermittently to the whole body of the donor or to a target tissue bed or a group of nerves. For example, such stimulation may be applied to a single limb of the donor such as a leg. A pair of skin electrodes may be used in this case such that the electrical current can travel from a first electrode to the second electrode. More than two electrodes may also be used. A suitable controller may be electrically coupled with skin electrodes and configured to manually or automatically deliver a remote conditioning treatment according to a predefined protocol. Suitable devices for applying electrical stimulation are described in the U.S. Pat. Nos. 6,023,642 and 5,183,041 incorporated herein in their respective entireties by reference.

Remote conditioning treatment protocol may specify duration of applying and withdrawal of the electrical stimulation, which may vary from about 1 second to about 2 hours at a time. In further embodiments, the duration of applying the electrical stimulation as well as duration for recovery and biological adaptation when the electrical stimulation is withdrawn may be 1 sec; 5 sec; 20 sec; 30 sec; 45 sec; 1 min; 2 min; 3 min; 5 min; 10 min; 15 min; 20 min; 30 min; 45 min; 60 min; 90 min; 120 min or any time inbetween.

The controller may also be programmed to apply between 2 and 20 cycles of such electrical stimulation. In embodiments, the controller may be programmed to automatically apply these electrical stimulation cycles consecutively 2 times; 3 times; 4 times; 5 times; 6 times; 10 times; 15 times; 20 times or any other number of times inbetween. Electrical parameters of this stimulation may include the extent of electrical current applied to the donor (which may vary from about 10 mA to about 500 mA); voltage (which may vary from about 1 V to 150 V); frequency (which may vary from 0 to about 500 Hz); and duty cycle (which may vary from about 10 percent to about 90 percent).

Remote conditioning of a donor may further be applied using techniques and devices described in the US Patent Application Publication Nos. 2009/0220585; 2010/0292755; and 2013/0317581, all of which are incorporated herein by reference in their respective entireties. Once remote conditioning is completed, the donor may proceed to donate blood or subject the blood for extracting remote conditioning substances as described elsewhere herein.

Exposure to light may be conducted using various light wavelengths from infrared, to near-infrared, to visible light, to ultraviolet spectrum. Single wavelength, multiple wavelengths or ranges of wavelengths may be used for this purpose. The source of suitable light may be one or more lamps, LEDs, lasers or other known devices emanating light.

Specific tissue beds may be used for intermittent application of light. In embodiments, tissues with high concentration of mitochondria may be more suitable for this purpose as mitochondria is known to participate in protective mechanisms of remote conditioning. More specifically, muscles and brain neurons may be used for light exposure. In case of the brain, a helmet may be provided containing a plurality of LED or laser light sources and configured to fit around the head of the donor. Near-infrared or red light may be used for intermittently and non-invasively applying a remote conditioning intervention to the donor.

In embodiments, light exposure may be applied for a predefined period of time ranging from about 1 minute to about 120 minutes. In further embodiments, the duration of light exposure per cycle may be the same or different between the cycles and may be 1 min; 3 min; 5 min; 10 min; 20 min; 30 min; 45 min; 60 min; 90 min, 120 min or anytime inbetween. The periods of biological recovery when the light is turned off may also range between about 1 min and about 120 min. in embodiments, the duration of light withdrawal may be the same or different between the cycles and may be 1 min; 3 min; 5 min; 10 min; 20 min; 30 min; 45 min; 60 min; 90 min, 120 min or anytime inbetween.

The intensity of light and other light characteristics may be selected to be effective in propagating stress to the target tissue but yet not cause any long-term or permanent tissue damage—and in that sense they may be considered sub-lethal. The number of cycles of light exposure may be between 2 and 20 cycles. In embodiments, the controller configured to turn the lights ON and OFF may be programmed to automatically activate cycles of light exposure consecutively 2 times; 3 times; 4 times; 5 times; 6 times; 10 times; 15 times; 20 times or any other number of times inbetween. In other embodiments, different clusters of lights may be activated or turned off at various times so as to apply intermittent light exposure to various tissue beds in a parallel or an overlapping manner.

Radiation exposure may be conducted on a repeated and intermittent basis to a target tissue bed or the whole body of the donor as yet another biological stress. While other types of radiation may be useful such as radionuclide, ionizing radiation may be preferred for the purposes of this invention and specifically the X-Ray gamma radiation may be useful as its biological effects are better documented in the literature.

As is generally suggested elsewhere in this description, the dosage of each individual cycle of remote conditioning may be selected to be at least strong enough to cause a biological adaptation response and yet not exceed the threshold of causing lasting or permanent tissue damage, such as exceeding about 3-5 Gy (300 to 500 rad). For radiation exposure, radiation doses to the patient may depend on the size of the patient as well as length of the procedure, with exemplary skin dose rates ranging from about 5 mGy/min to about 100 mGy/min. In embodiments, the rate of radiation dose may be 5, 10, 15, 20, 30, 40, 50, 60, 70, 80, 90, 100 mGy/min or any level therebetween. Exposure times for each cycle may range from about 5 min to about 75 min. In embodiments, the exposure time may be 5, 10, 15, 20, 30, 40, 50, 60, 70, 75 min or any duration therebetween. The period of rest and biological adaptation inbetween radiation exposure may vary from 5 min to several days and even weeks. In embodiments, the period of withdrawal of radiation may be 5, 10, 15, 20, 30, 40, 50, 60, 90, 120, 180 min or any duration therebetween. In other embodiments, the duration of rest may be 1, 2, 3, 4, 5, 6, 7, 10, 14, 21 days or any duration therebetween. The number of exposure cycles may range from two to 10 and may be 2, 3, 4, 5, 6, 7, 8, 9, or 10 cycles.

Toxic substance exposure on a repeated basis is yet another example of a biological stress used to induce remote conditioning according to the present invention. a variety of toxic substances in sublethal doses may be ingested, inhaled, injected or otherwise administered to the donor. Toxic substances with known biological effects may be preferred for use for the method of the invention as compared with other less known toxic substances. Examples of toxic substances with known biological effects are inhalation of smoke, injection of chemical therapy agents, narcotics, etc.

Pharmacological substance to simulate effects of remote conditioning or triggering temporary adaptive biological responses thereto may also be administered to the donor for the method of the present invention. As opposed to previously described biological stresses that may be applied two times or more, a single or several pharmacological substances may be administered only once to the patient in a dosage sufficient to cause a remote conditioning effect. In embodiments, such substance may also be administered several times.

Examples of a pharmacological substance useful for the purpose of the invention may include an anesthetic agent, such as propofol, sevoflurane, or another volatile anesthetic. Other examples of such pharmacological substances include adenosine, acadesine, bradykinin-2, opioid, $CB_2$, endocannabinoid, cyclosporine, angiotensin-1, nicorandil, prostaglandil, metoprolol, $H_2O_2$, diazoxide, erythropoietin, $Na^+$—$H^+$ exchange inhibitors, cariporide, and various other compounds that are described in the literature as mimicking the effects of remote conditioning or activating at least in part some of the mechanisms involved therein. Further examples of such pharmacological substances may be found in an article by I. Andreadou et al. entitled "Alternative Pharmacological Interventions that Limit Myocardial Infarction", published in 2008 in Current Medical Chemistry; as well as an article by Maurits T. Dirksen et al entitled "Reperfusion injury in humans: A review of clinical trials on reperfusion injury inhibitory strategies", published in Cardiovasc Res (2007) 74 (3): 343-355; and further in an article by D J Hausenloy entitled "Myocardial ischemia-reperfusion injury: a neglected therapeutic target" as published in the Journal of Clinical Investigation in 2013; 123(1):92-100, all of these articles are incorporated herein by reference in their respective entireties.

In other embodiments, several spaced apart injections of muscle-stimulating drugs may be used as a biological stress for the methods of the invention. For example, spaced apart injections of epinephrine may be used to stimulate the heart several times to trigger release of remote conditioning substances.

In addition to mimicking the biological stress itself, pharmacological substances may be selected to cause the same or similar biological adaptive reaction to such stress without applying the biological stress itself. Such adaptive reaction may be reducing the levels of released reactive oxygen species, upregulating the release of RISK or SAFE kinases, preventing the opening of the mitochondrial permeability transition pores, normalizing levels of certain microRNAs (such as microRNA-1, microRNA-133a, microRNA-133b, microRNA-144, microRNA-338-3p), activating signal transducer and activator of transcription 3 (STAT3), reducing inflammation, etc.

Donor Blood Collecting and Processing Considerations

Either arterial or venous blood or blood-derived products or substances may be used for the methods of the present invention. One advantage of collecting arterial blood or extracting biologically active preparations containing humoral factors or remote conditioning substances from arterial blood may be that more remote conditioning substances may be present therein.

Once the donor has undergone remote conditioning procedure and within the time frames discussed above, whole arterial or venous blood may be collected from the donor, which contains at least one remote conditioning substance. Such blood may be used immediately and directly by a transfusion to a treatment subject. In other embodiments, such blood may be stored for future use, for example after 1 hr, 2 hrs, 3 hrs, 6 hrs, 12 hrs, 24 hrs, 2 days, 3 days, 4 days, 7 days, or several weeks after blood collection. Such storage may follow routine blood storage protocols described elsewhere.

One useful health benefit derived from remote conditioning may be improved red blood cells viability. Red blood cells are known to undergo certain degradation while in storage, a phenomenon that can be broadly described as "storage lesion". Subjecting a donor to remote conditioning prior to blood collection may improve storage tolerance of red blood cells and allow for their longer storage duration without compromising their viability once transferred to a treatment subject. Another health benefit may be reduced hemolysis, a known complication of red blood transfusions.

In embodiments, improved viability of other blood components and blood-derived products may also be caused by performing remote conditioning on a donor subject prior to blood collection therefrom.

In yet other embodiments, collected whole blood from a preconditioned donor may be processed to derive a biologically active preparation therefrom including removal of pathogens and optional separation into various blood components, for example red blood cells may be separated from platelets and further from plasma. Such blood components may be then separately stored and used individually at a future point of time for infusions for the treatment subject.

In other yet embodiments, the biologically active preparation may be a serum prepared from collected whole blood of the donor after applying remote conditioning thereto. Serum may be prepared by removing red and white blood cells as well as removing fibrinogens from remaining plasma. Serum may include all other proteins that are not used in blood clotting (coagulation) and all the electrolytes, antibodies, antigens, hormones, and any exogenous substances such as remote conditioning substances. Once prepared, such serum may be used directly to infuse into the treatment subject or may be stored (including freezing) for future use.

In embodiments, the serum may be further processed extracorporeally to extract one or more of remote conditioning substances. Various blood effluent processing methods may be used for the production of the biologically active preparation of the invention including serum filtration, chromatography including reverse-phase chromatography, hydrophobic elution, dialysis, liquid exchange through a porous or electrically charged membrane, centrifugation, plasmapheresis or electrophoresis. In embodiments, particles with molecular weight less than about 100 kiloDaltons (kD) may be separated from serum and stored for future use. In other embodiments, particles with molecular weight less than 90 kD, 80 kD, 70 kD, 60 kD, 50 kD, 40 kD, 30 kD, 20 kD, 15 kD, 10 kD or any molecular weight inbetween along with surrounding fluids may be separated from serum or whole blood and stored for future use to deliver a health benefit of remote conditioning to the treatment subject. In further embodiments, after separating particles less than a predetermined molecular weight ranging from about 10 kD to about 100 kD, a second processing step may be added to remove all fluids and particles less than about 2 kD such that remaining substances may be further used to produce the biologically active preparation of the present invention. In embodiments, extraction of all particles within a range of molecular weight from about 2 kD to about 10 kD from donor blood or blood—derived products may be used for producing the biologically active preparation of the invention. In further embodiments, additional processing may be applied to separate only hydrophobic subset of particles for further inclusion in the biologically active preparation of the invention.

The above molecular weight ranges may be applicable to remote conditioning substances released in the time period associated with the first window of protection. The second window of protection may be associated with certain protein-based remote conditioning substances, which may be larger in molecular weight and therefore may require different suitable target range of processing. In embodiments, processing of conditioned donor blood or blood-derived product during the time period associated with the second window of protection may be done to separate protein-based remote conditioning substances. Such protein-based remote conditioning substances may range in molecular weight from about 50 kD to about 1,000 kD.

Once processed using blood, blood effluent, blood perfusate or other blood-derived fluids, such particles and fluids containing remote conditioning substances may be converted into the biologically active preparation in the form of a fluid, powder or in another acceptable pharmacological form. Commonly used pharmacological preservatives and other additives may be used to stabilize and preserve the health benefit properties of separated remote conditioning substances.

Following traditional human blood donation practices, only one unit of blood may be collected from each donor. That amount of blood may or may not contain enough remote conditioning substances to provide sufficient health benefit when administered to the treatment subject. To increase the volume of collected remote conditioning substances, blood from the conditioned donor may be processed for extraction of remote conditioning substances and then returned to the donor. Such processing may be done using an indwelling catheter configured to separate the remote conditioning substances from surrounding blood and remove them from the blood stream of the donor. In other embodiments, blood may be channeled out of the donor's body, processed extracorporeally and then returned back to the donor so that remote conditioning substances may be extracted from a larger blood volume without depriving the donor or the rest of the blood components.

Extracorporeal blood processing may be done using various blood processing methods including for example blood filtration, chromatography including reverse-phase chromatography, hydrophobic elution, dialysis, liquid exchange through a porous or electrically charged membrane, centrifugation, plasmapheresis or electrophoresis. Blood dialysis or plasmapheresis may be advantageous to extract remote conditioning substances as they allow separation of particles of desired molecular weight, such as less than about 10 kD, 15 kD, 20 kD, 30 kD, 40 kD, 50 kD, 60 kD, 70 kD, 80 kD, 90 kD, 100 kD or any molecular weight inbetween. After extraction of such particles, remaining blood may be returned to the donor. Dialysate or perfusate of blood may be further processed to concentrate remote conditioning substances therein. In further embodiments, after separating particles less than a predetermined molecular weight ranging from about 10 kD to about 100 kD, a second processing step may be added to remove all fluids and particles less than about 2 kD such that only remaining substances may be further used to produce the biologically active preparation of the present invention. In embodiments, extraction of all particles within a molecular weight range from about 2 kD to about 10 kD from donor blood or blood—derived products may be used for producing the biologically active preparation of the invention. In further embodiments, additional processing may be applied to separate only hydrophobic subset of particles for further inclusion in the biologically active preparation of the invention.

In further yet embodiments, when blood collection or processing is done during the second window of protection, the target molecular weight range for extracting protein-based remote conditioning substances may be increased to constitute a desired range of molecular weight from about 50 kD to about 1,000 kD.

Various blood-compatible filters or membranes may be used to separate at least one remote conditioning substance. Such filters or membranes may have a predefined pore size corresponding to the desired molecular weight of the particles to be separated from blood. In other embodiments, such filters may have a membrane with a suitable electric charge on its surface to attract desired particles. Other designs may allow separation of desired hydrophobic substances from all others. In embodiments, blood or a blood product may be pressurized to flow through the filter, allowed to flow based on natural gravity or capillary action, or may be pulled through the filter by applying negative pressure on the outlet thereof.

Duration of intracorporeal or extracorporeal blood processing may be selected to be from about 5 minutes to about 3 hours. In other embodiments, such duration may be 5 min, 10 min, 15 min, 20 min, 30 min, 45 min, 60 min, 90 min, 120 min, 150 min, 180 min or any time inbetween. In other embodiments, such duration may be adjusted and truncated once the desired amount of remote conditioning substances is collected or extracted.

The term "donor" is used herein to include a human donor as well as a non-human donor. While a variety of animals, birds and fish may be used as donors for the purposes of the invention, using of larger animals for collecting remote conditioning substances may present an opportunity for inexpensive, rapid processing and accumulation of remote conditioning substances. Such remote conditioning substances that may be used to treat humans or other animals. In embodiments, non-human mammalian species and specifically large mammalian species may be used as donors for collecting remote conditioning substances. One advantage of using a large mammalian animal for the present invention is that more than one unit of blood may be collected from a single animal. Large blood quantity may be advantageous for extracting greater volumes of remote conditioning substances.

In embodiments, larger farm animals may be used as donors for the methods of the invention, including sheep, pigs, cows, horses, donkeys, etc. Such animals are readily accessible and easy to work with. Remote conditioning may be applied to these animals using the same methods as described above, for example by intermittently placing tourniquets about one or more limbs of the animal. Once remote conditioning is complete, blood collection or extraction of remote conditioning substances may be accomplished using the same or similar techniques as described above. Blood or serum from conditioned animal donors may include additional processing steps to make it compatible for future human use.

Pooling of blood, blood components including serum, or extracted remote conditioning substances to make the biologically active preparation of the invention may be conducted using a group of donors. Using more than one donor may be implemented to increase the volume of remote conditioning substances contained therein. In embodiments, at least one, several or all donors from the group of donors may be subjected to remote conditioning prior to collecting of donor blood or extracting remote conditioning substances. As with regular blood, pooling must be done following suitable practices of combining blood or blood products compatible with each other so as not to subject the treatment subject to an increased risk of inflammatory response upon the use of such pooled blood or biologically active preparations derived therefrom.

The use of blood or a blood product derived from a conditioned donor may include direct injection into the treatment subject or adding thereof to another blood or blood product and later administering thereof to the treatment subject via injection or transfusion.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of obtaining from a donor of blood or a blood product derived therefrom for subsequent transfusion, said blood or said blood product containing at least one remote conditioning substance with properties to reduce inflammation or attenuate ischemia-reperfusion injury in a recipient in need of such transfusion, comprising in the following order,
    (a) Providing a blood donor,
    (b) Stressing the blood donor by ischemic conditioning comprising;
        (i) Intermittently occluding circulation, partially or completely, to a body part of the blood donor for a period of 30 seconds to 20 minutes without causing irreversible damage to the body per,
        (ii) Intermittently restoring circulation to the body part for a period of 30 seconds to 20 minutes,
        (iii) Repeating the occluding and the restoring of steps (i) and (ii) 2-10 times,
    (c) Collecting blood from the blood donor subsequent to the above steps,
    (d) Optionally storing and/or processing the collected blood to produce said blood product, and
    (e) Administering the collected blood or said blood product to the recipient.

2. The method as in claim 1, wherein said step (c) of collecting blood is conducted within a first time period of a first window of protection or a second time period of a second window of protection caused by said ischemic conditioning.

3. The method as in claim 2, wherein said first time period starting immediately after completion of said ischemic conditioning and lasting for six hours afterwards, said second time period starting about 24 hours after completion of said ischemic conditioning and lasting for about 96 hours afterwards.

4. The method as in claim 1, wherein said optional step (d) of processing the collected blood comprises a step of an extracorporeal processing of the blood of the blood donor.

5. The method as in claim 4, wherein said step of extracorporeal processing of the blood of the blood donor further comprising a step of filtering, centrifugation, electrophoresis or liquid exchange through a porous membrane.

6. The method as in claim 4 further comprising a step of returning said blood to the blood donor when said blood donor is said recipient.

7. The method as in claim 2, wherein said step (d) further comprising a step of extracting blood components with molecular weight smaller than 20 kD when said blood is collected during said first time period or extracting blood components with molecular weight ranging from about 50 kD to about 1,000 kD when said blood is collected during said second time period.

8. The method as in claim 4, wherein said step of extracorporeal processing of the blood of said donor is conducted using an extracorporeal blood dialysis process.

9. The method as in claim 1, wherein said optional step (d) of storing said collected blood or said blood product extends for at least 24 hours between said step (c) of collecting blood and said step (e) of administering thereof to said recipient.

10. The method as in claim 1, wherein said blood product containing said at least one remote conditioning substance is selected from the group consisting of plasma, serum, red blood cells, platelets, and a biologically active preparation thereof.

11. The method as in claim 1 further comprising a step of pooling blood, pooling blood products derived therefrom or pooling remote conditioning substance extracted from a plurality of blood donors, at least one of said donors being subjected to ischemic conditioning.

12. The method as in claim 1 further including a step of adding said extracted remote conditioning substance to the blood or the blood-derived product derived from the same donor, another donor or a group of donors.

* * * * *